(12) United States Patent
Chen et al.

(10) Patent No.: US 8,726,933 B2
(45) Date of Patent: May 20, 2014

(54) PRESSURE CONTROL VALVE

(75) Inventors: Geng Chen, Fengtai Science (CN);
Chang Jin, Fengtai Science (CN)

(73) Assignee: Beijing Aeonmed Co, Ltd., Beijing (CN)

( * ) Notice: Subject to any disclaimer, the term of this patent is extended or adjusted under 35 U.S.C. 154(b) by 379 days.

(21) Appl. No.: 13/264,688

(22) PCT Filed: Apr. 15, 2010

(86) PCT No.: PCT/CN2010/071796
§ 371 (c)(1),
(2), (4) Date: Oct. 14, 2011

(87) PCT Pub. No.: WO2010/118693
PCT Pub. Date: Oct. 21, 2010

(65) Prior Publication Data
US 2012/0032101 A1    Feb. 9, 2012

(30) Foreign Application Priority Data
Apr. 15, 2009 (CN) .......................... 2009 1 0082393

(51) Int. Cl.
*F16K 35/10* (2006.01)
*F16K 21/04* (2006.01)
*F16K 37/00* (2006.01)

(52) U.S. Cl.
USPC .............................. 137/524; 137/557; 251/96

(58) Field of Classification Search
USPC ..................................... 137/524, 557; 251/96
See application file for complete search history.

(56) References Cited

U.S. PATENT DOCUMENTS 1,467,671 A * 9/1923 Kaiser ........................... 137/224
1,584,934 A * 5/1926 Harris ............................ 137/225
(Continued)

FOREIGN PATENT DOCUMENTS

CN        2176469 Y      8/1994
CN        1162778 A      10/1997
(Continued)

OTHER PUBLICATIONS

International Search Report of PCT, International Application No. PCT/CN2010/071796, dated Jul. 5, 2010, 6 pages.
(Continued)

*Primary Examiner* — John K Fristoe, Jr.
*Assistant Examiner* — Daphne M Barry
(74) *Attorney, Agent, or Firm* — Barley Snyder

(57) ABSTRACT

The present invention discloses a pressure control valve comprising: a cylindrical valve body which has a bottom wall and a side wall, wherein the bottom wall is provided thereon with an air inlet communicating with a device whose pressure to be limited, the side wall is provided with at least one guiding pin, and the cylindrical valve body has air outlets communicating with an exhausting system; a valve core, which is provided within the cylindrical valve body and in air-tight cooperation with the air inlet; a traveling guiding bar, having a lower end connected to the valve core; a covering fitted rotatably or up-and-down movably over the cylindrical valve body, for driving the traveling guiding bar to rotate or move up-and-down; a spiral guiding member, which is fitted up-and-down movably over the traveling guiding bar and is provided on its outer surface with spiral grooves into which the at least one guiding pin can be inserted; a pressure spring, having one end pressed against the valve core and the other end standing against the spiral guiding member.

11 Claims, 21 Drawing Sheets

(56) References Cited

U.S. PATENT DOCUMENTS

| | | | | |
|---|---|---|---|---|
| 1,589,696 | A | * | 6/1926 | Holtz ............................. 251/223 |
| 2,321,679 | A | * | 6/1943 | Houston ....................... 137/524 |
| 3,013,790 | A | * | 12/1961 | Anderson et al. ............. 267/175 |
| 3,536,092 | A | | 10/1970 | Klasson |
| 4,545,405 | A | * | 10/1985 | LaBelle ........................ 137/524 |
| 5,294,093 | A | * | 3/1994 | Huveteau et al. ............. 251/263 |
| 5,839,436 | A | | 11/1998 | Fangrow, Jr. et al. |
| 5,950,623 | A | * | 9/1999 | Michell .................... 128/205.24 |
| 6,082,705 | A | | 7/2000 | Arvidsson |
| 6,691,735 | B1 | * | 2/2004 | Harneit ......................... 137/524 |
| 7,481,219 | B2 | | 1/2009 | Lewis et al. |

FOREIGN PATENT DOCUMENTS

| | | |
|---|---|---|
| CN | 2730399 Y | 9/2004 |
| CN | 2915082 Y | 6/2006 |
| CN | 200939293 Y | 8/2006 |
| CN | 101219249 A | 7/2008 |
| GB | 2250801 A | 6/1992 |

OTHER PUBLICATIONS

SIPO Examination Report 6 pages, dated May 1, 2013.

* cited by examiner

PRESSURE CONTROL VALVE

RELATED APPLICATION DATA

This application is a national stage filing of PCT International Application No. CN2010/071796, filed Apr. 15, 2010 which claims priority under 35 U.S.C. §119 to Chinese Patent Application No. 200910082393.4, filed Apr. 15, 2009.

FIELD OF INVENTION

The present invention relates to a pressure control valve.

BACKGROUND

In an anesthesia operation, an anesthetic machine is an important apparatus with which an anesthetist makes a patient to be in narcosis, so as to treat the patient. An anesthetic loop is an important device indispensable for an anesthetic machine to achieve cycle closed anesthesia. In the case that the anesthetic loop is ventilated manually, if the pressure is too high in the loop, it causes the pressure in a patient's lung to be too high, harming the patient to a certain extent, but if the pressure is too low, it can not meet the requirement of supplying air. Also, the applied pressure is different depending on different situations and if the pressure in the air path is constant, it can not meet the requirement of varying pressure. A pressure control valve is provided on the anesthetic loop, for limiting and positioning a pressure value.

During realizing the present invention, the present inventor found that the existing pressure control valve was not enough to limit and position the pressure value accurately.

SUMMARY

The present invention provides a pressure control valve, aiming at solving the above problems.

To this end, the present invention provides a pressure control valve comprising: a cylindrical valve body which has a bottom wall and a side wall, wherein the bottom wall is provided thereon with an air inlet communicating with a device whose pressure to be limited, the side wall is provided with at least one guiding pin, and the cylindrical valve body has air outlets communicating with an exhausting system; a valve core, which is provided within the cylindrical valve body and in air-tight cooperation with the air inlet; a traveling guiding bar, having a lower end connected to the valve core; a covering fitted rotatably or up-and-down movably over the cylindrical valve body, for driving the traveling guiding bar to rotate or move up-and-down; a spiral guiding member, which is fitted up-and-down movably over the traveling guiding bar and is provided on its outer surface with spiral grooves into which the at least one guiding pin can be inserted; a pressure spring, having one end pressed against the valve core and the other end standing against the spiral guiding member.

Preferably, the pressure control valve further comprises a fine-adjusting structure including: an index plate fixed on the top of the traveling guiding bar and driven by the covering, and an elastic device provided at the top end of the cylindrical valve body, wherein the index plate has a positioning face which is in contact with the elastic device and the positioning face is distributed with pits or holes for the positioning of the elastic device.

Preferably, the positioning face of the index plate has an annular bottom surface, a step surface and a transition inclined surface located between the annular bottom surface and the step surface, wherein one end side of the annular bottom surface is provided with a first positioning side face, and one end of the step surface is provided with a second positioning side face.

Preferable, the elastic device comprises a top pin and a pillar spring located under the top pin.

Preferably, the covering comprises an upper cover and an outer casing fixedly connected with the upper cover, wherein the outer casing is fitted rotatably or up-and-down movably over the cylindrical valve body, and the outer circumference surface of the index plate is provided with at least one mating notch, and the outer casing has driving key(s) inserted into the at least one mating notch.

Preferably, the top face of the index plate is flush with the top end of the outer casing, and a pressing board is provided between the top face of the index plate and the inner top surface of the upper cover, with the pressing board fixed together with the index plate.

Preferably, the cylindrical valve body is at its upper portion provided with a restoration spring base, the outer casing is provided on its inner wall with an annular positioning flange, and a restoration spring is provided between the restoration spring base of the cylindrical valve body and the annular positioning flange of the outer casing.

Preferably, the traveling guiding bar has a first cavity therein, the valve core has a threaded rod which is inserted into the end of the first cavity, and the threaded rod is connected with a valve core nut positioned within the first cavity and is fastened by a first fastening screw.

Preferably, the end of the spiral guiding member contacting with the pressure spring is formed in a concave shape, so as to form a pressure spring base hole.

Preferably, the outer surface of the traveling guiding bar has at least one traveling guiding bar positioning face extending along the axial direction, the spiral guiding member has therein a second cavity which in turn has therein at least one spiral guiding member positioning face matching with the at least one traveling guiding bar positioning face.

Preferably, the traveling guiding bar is provided at its top with connection faces, the index plate is provided with screw holes, and the index plate is fixed to the connection faces of the traveling guiding bar by second fastening screws.

Thanks to the following facts: the cylindrical valve body has the air inlet communicating with a device whose pressure is to be limited; the covering drives the traveling guiding bar to rotate or move up- and down; the spiral guiding member is fitted up-and-down movably over the traveling guiding bar; a pressure spring has one end pressed against the valve core and the other end standing against the spiral guiding member; the index plate is fixed on the top of the traveling guiding bar and driven by the covering; the elastic device is provided at the top end of the cylindrical valve body; and the index plate has the positioning face which is in contact with the elastic device, the valve core in air-tight cooperation with the air inlet and provided in the cylindrical valve body is pressed or released by the spiral guiding member. Using the above structure, the valve core in air-tight cooperation with the air inlet and provided in the cylindrical valve body is pressed or released by the spiral guiding member, which can adjust the press-down extent of the valve core by combining the rotation and linear movement. Furthermore, the adjustments of the index plate and the elastic device can more accurately adjust the pressure of the device whose pressure is to be limited, such that the pressure control valve can position and limit a pressure value more simply, effectively and accurately. At the same time, the covering, no matter what position it is located, can be made to move upwards, driving the traveling guiding bar and the valve core to move upwards, such that the valve core is disengaged from the air inlet, so as to achieve the function of quickly exhausting air.

Apart from the above mentioned objects, features and advantages, the present invention can bring about other objects, features and advantages, which are further described in detail hereinafter in conjunction with figures.

BRIEF DESCRIPTION OF THE DRAWINGS

The drawings described herein provide a further understanding of the present invention and constitute a part of the application. The exemplary embodiments of the present invention and the description thereof are used for explaining the present invention, rather than limiting the present invention unduly. In the drawings.

DETAILED DESCRIPTION OF THE EMBODIMENTS

Hereinafter, the present invention will be described in detail in connection with the drawings and embodiments.

Figure 1:
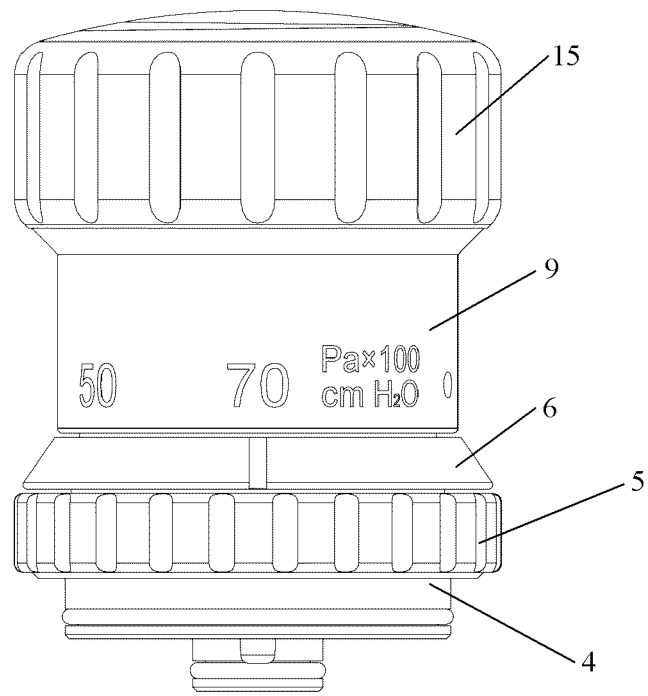
FIG. 1 shows a front view of the outer structure of a pressure control valve according to an embodiment of the present invention.
Figure 2:
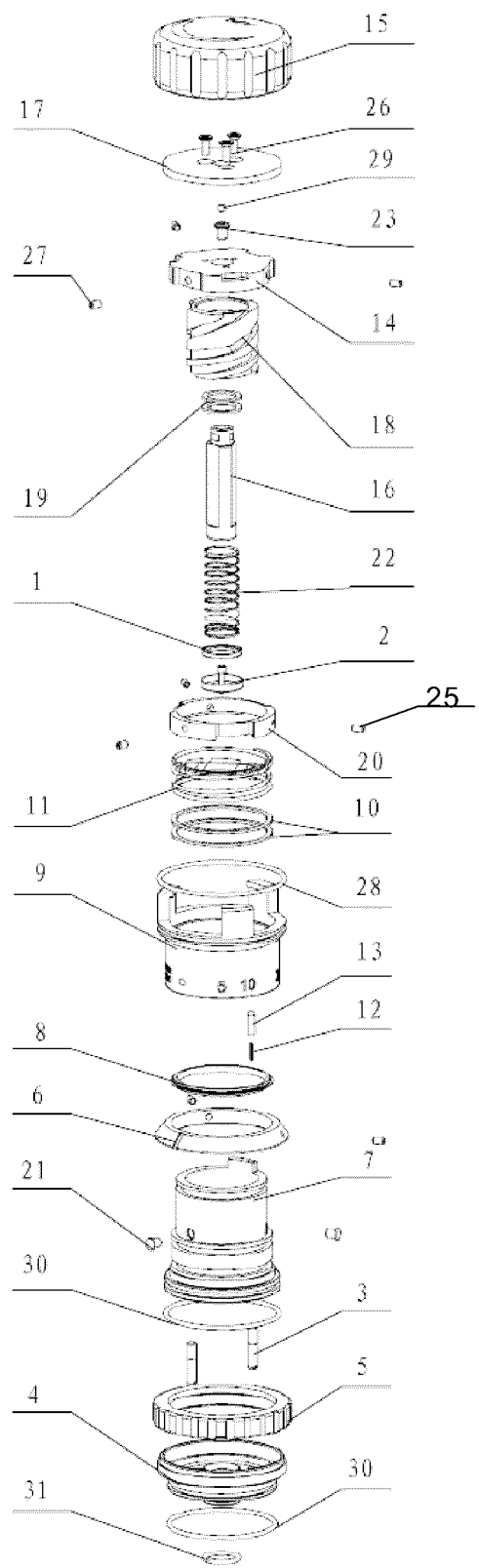
FIG. 2 shows an exploded view of the pressure control valve in FIG. 1.
Figure 3:
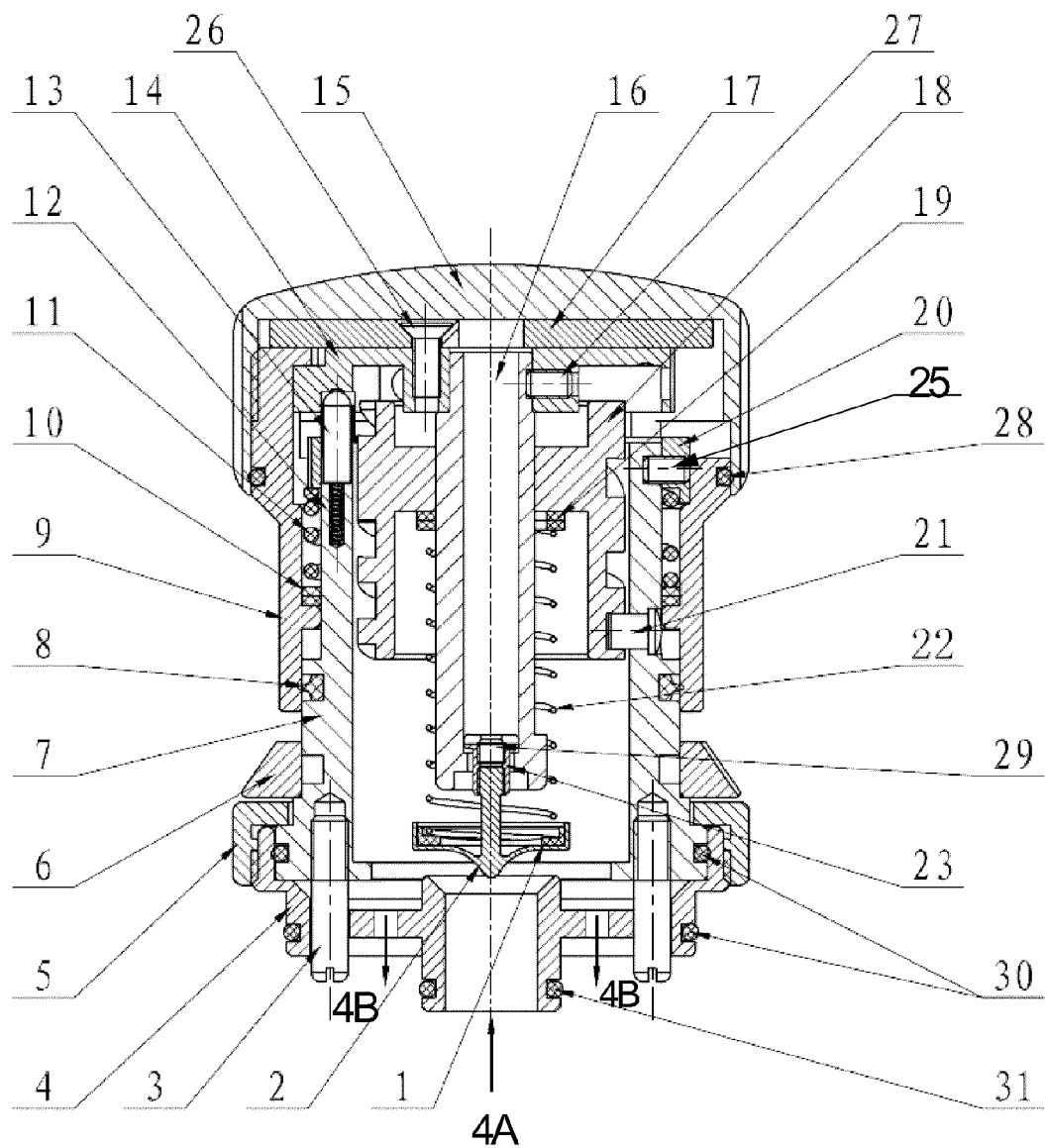
FIG. 3 shows a sectional view of the pressure control valve in FIG. 1, wherein a scale value indication plate is set to Zero.
Figure 4:
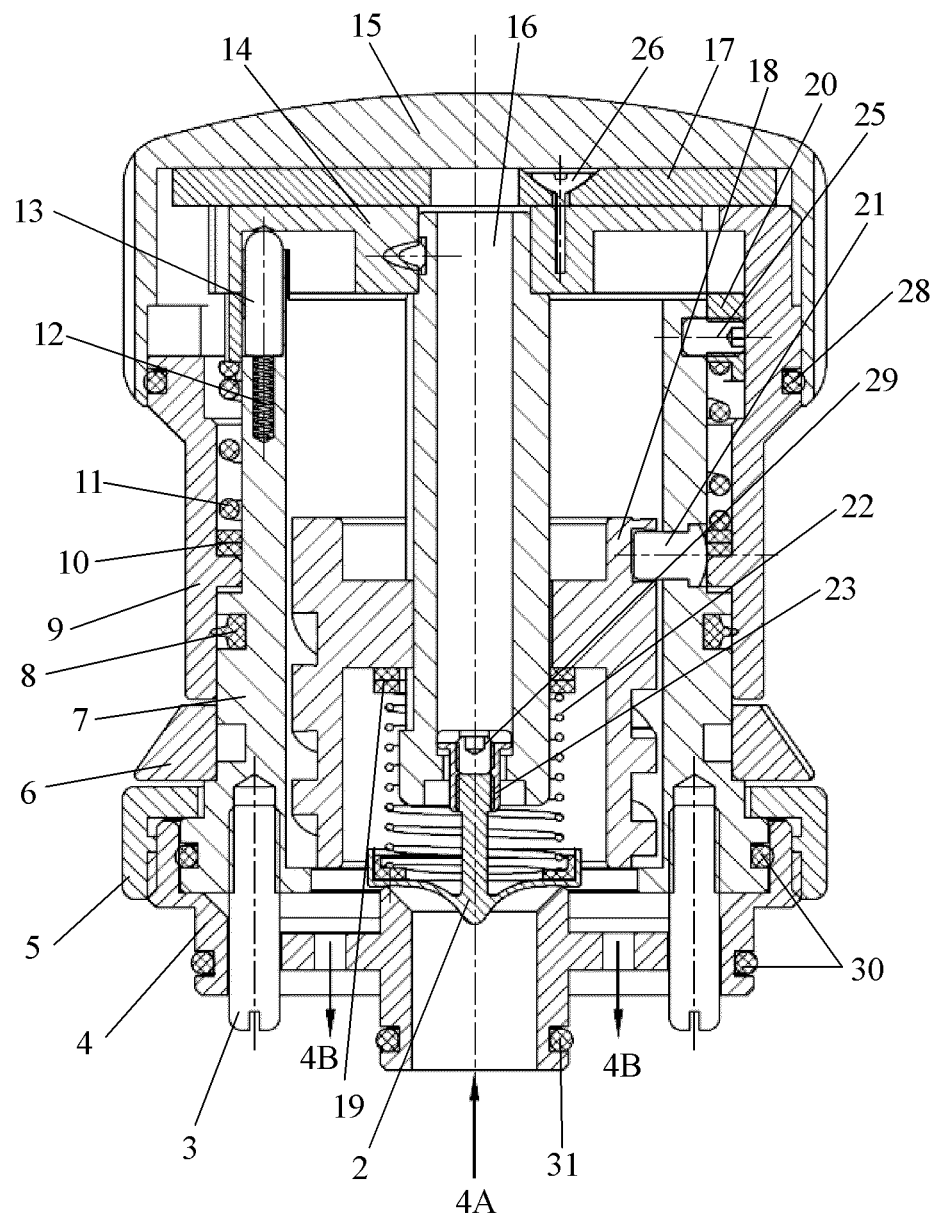
FIG. 4 shows a sectional view of the pressure control valve in FIG. 1, wherein the scale value indication plate is set to a maximum value.

A pressure control valve according to the present invention can be used on an anesthetic machine, but not limited thereto, and also can be used on other devices. FIG. 1 shows the front view of outer structure of the pressure control valve according to an embodiment of the present invention. FIG. 2 shows an exploded view of the pressure control valve in FIG. 1. FIGS. 3 and 4 show sectional views of the pressure control valve in FIG. 1 under two conditions. Referring to FIGS. 1-4, it is shown that the figures illustrate the following components: a cylindrical valve body (including a valve seat 4 and an inner casing 7 co-axially fixed on the valve seat 4); a locking sleeve 20, fixedly fitted over the inner casing 7; an index plate 14 located over the inner casing 7 and provided co-axially with the inner casing 7; a covering (including an outer casing 9 and an upper cover 15); a pressing board 17 covering over the outer casing 9 and the index plate 14; a spiral guiding member 18 co-axially provided in the inner casing 7; a traveling guiding bar 16 co-axially provided in the spiral guiding member 18; a valve core 2 co-axially provided at the lower end of the traveling guiding bar 16; the upper cover 15 surrounding the outer casing 9 and the pressing board 17; a first sealing member 31; second sealing members 30; a damping washer 8; a fourth sealing member 28; a threaded sleeve 5; a scale value indication plate 6 and so on.

Meanwhile, the pressure control valve according to the embodiment of the present invention comprises: a cylindrical valve body having a bottom wall and a side wall, wherein the bottom wall is provided thereon with an air inlet 4A communicated with a device whose pressure is to be limited and the side wall is provided with at least one guiding pin 21; a valve core 2, which is provided within the cylindrical valve body and in air-tight cooperation with the air inlet 4A; a traveling guiding bar 16, having a lower end connected to the valve core 2; a covering fitted rotatably or up-and-down movably over the cylindrical valve body, so as to drive the traveling guiding bar 16 to rotate or move up-and-down; a spiral guiding member 18, which is fitted up-and-down movably over the traveling guiding bar 16 and is provided on its outer surface with spiral grooves into which the at least one guiding pin 21 can be inserted; and a pressure spring 22, having one end pressed against the valve core 2 and the other end standing against the spiral guiding member 18. The pressure control valve further comprises a fine-adjusting structure including an index plate 14 fixed on the top of the traveling guiding bar 16 and driven by the covering; and an elastic device which is provided at the top end of the cylindrical valve body, wherein the index plate 14 has a positioning face which is in contact with the elastic device and the positioning face is distributed with pits or holes for positioning the elastic device.

Thanks to the following facts: the cylindrical valve body has the air inlet communicating with the device whose pressure to be limited; the covering is fitted rotatably over the cylindrical valve body and drives the traveling guiding bar to rotate, and at the same time brings the spiral guiding member to rotate therewith, wherein the spiral guiding member can move up-and-down with respect to the traveling guiding bar while being rotating; the pressure spring has one end pressed against the valve core and the other end against the spiral guiding member; the index plate is fixed on the top of the traveling guiding bar and driven by the covering; the elastic device is provided at the top end of the cylindrical valve body; and the index plate has the positioning face which is in contact with the elastic device, the valve core in air-tight cooperation with the air inlet and provided in the cylindrical valve body is pressed or released by the spiral guiding member, wherein the above components can adjust the press-down extent of the valve core by combining the rotation and linear movement. The adjustments of the index plate and the elastic device can accurately adjust the pressure of the device whose pressure to be limited, such that the pressure control valve can position and limit a pressure value more simply, effectively and accurately, and at the same time, the covering, no matter what position, can be made to move upwards, driving the traveling guiding bar and the valve core to move upwards, such that the valve core is disengaged from the air inlet, so as to achieve the function of quickly exhausting air.

Hereinafter, the structures of individual components of the pressure control valve according to the present invention will be described in detail.

Figure 29:
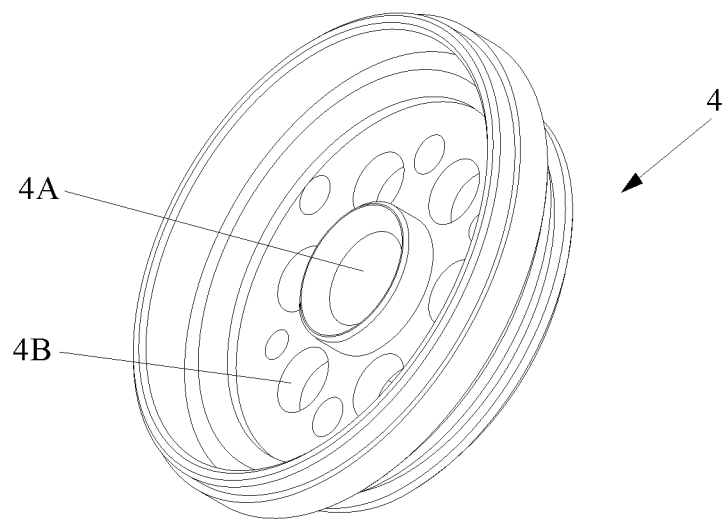
FIG. 29 shows a perspective view of a valve seat in FIG. 2.
Figure 30:
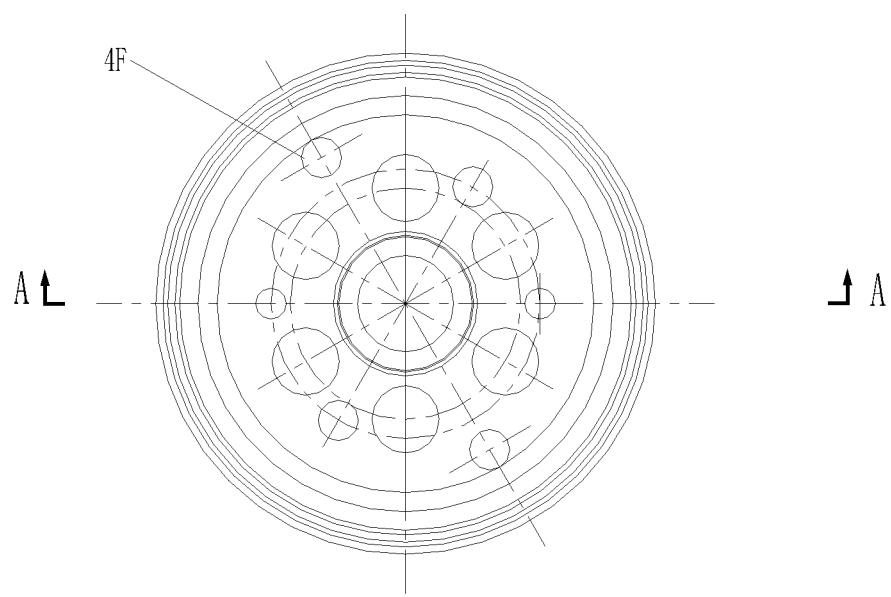
FIG. 30 shows a top view of the valve seat in FIG. 29.
Figure 31:
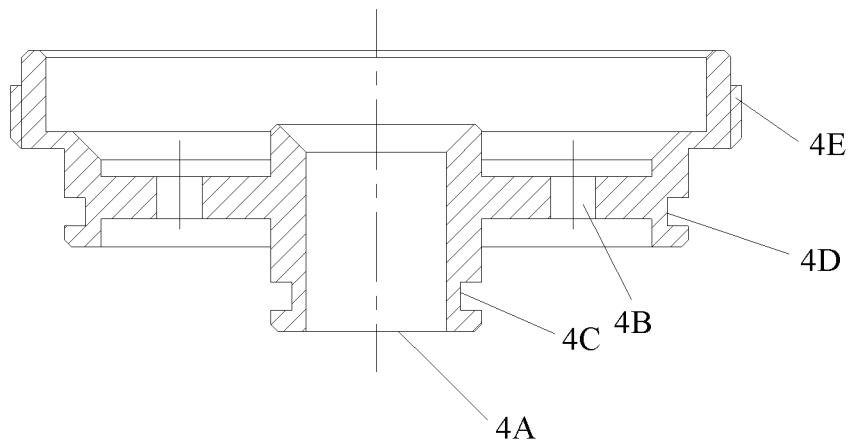
FIG. 31 shows a sectional view of the valve seat in FIG. 29.

The cylindrical valve body comprises a valve seat 4 and an inner casing 7, wherein the valve seat 4 is provided with the air inlet 4A communicating with a device whose pressure to be limited, and the inner casing 7, in cylindrical shape and fixed to the valve seat 4, is provided with at least one guiding pin 21. FIG. 29 shows the perspective view of the valve seat in FIG. 2. FIG. 30 shows the top view of the valve seat in FIG. 29. FIG. 31 shows the sectional view of the valve seat in FIG. 29. As shown in FIGS. 29, 30 and 31, the valve seat 4 is provided with an air inlet 4A and air outlet(s) 4B on the bottom side, wherein the number of the air inlets 4B is greater than one, i.e., may be more than one, so as to facilitate exhausting the air. The air inlet 4A and the air outlet(s) 4B are provided on the loop (i.e. the device whose pressure to be limited), for example, on the anesthetic loop. Obviously, the pressure control valve according to the present invention can applied to other kinds of the devices whose pressure to be limited. The cylindrical valve body is designed as split type, which facilitates the connection with the device whose pressure to be limited and the installation of the cylindrical valve body itself. Of course, the air inlet 4B is not limited to be provided in valve seat 4, and may be provided in the inner casing 7 or other components.

The valve seat 4 is, on the outer wall of its upper portion, provided with an outer thread 4E, so as to be threadedly connected with the threaded sleeve 5. The inner wall of the valve seat has a sealing edge extending surrounding the lower end of the inner wall, facilitating the sealing. As shown in FIGS. 3 and 4, a first sealing member 31 for sealing the air inlet 4A is provided at the air inlet 4A, for example, can be fitted in a slot 4C at the bottom of the air inlet 4A, and second sealing members 30 comprise a sealing member for isolating the inner casing 7 from the valve seat 4 and a sealing member for isolating the air outlet(s) 4B from the atmosphere, wherein these two sealing members may be for example sealing rings of the same or different type. The two sealing members included in the second sealing members 30 can be respectively fitted in a slot 4D of the valve seat 4 and a slot 74 of the inner casing 7. The valve seat 4 is provided with pin holes 4F which are used for fixedly connecting with the inner casing 7.

In operation, the valve seat 4 is connected with a device requiring pressure control, in which the constructions shown in FIGS. 3 and 4 can be employed, so as to achieve quick plugging and unplugging, and in addition a threaded structure may also be used for the connection.

Figure 7:
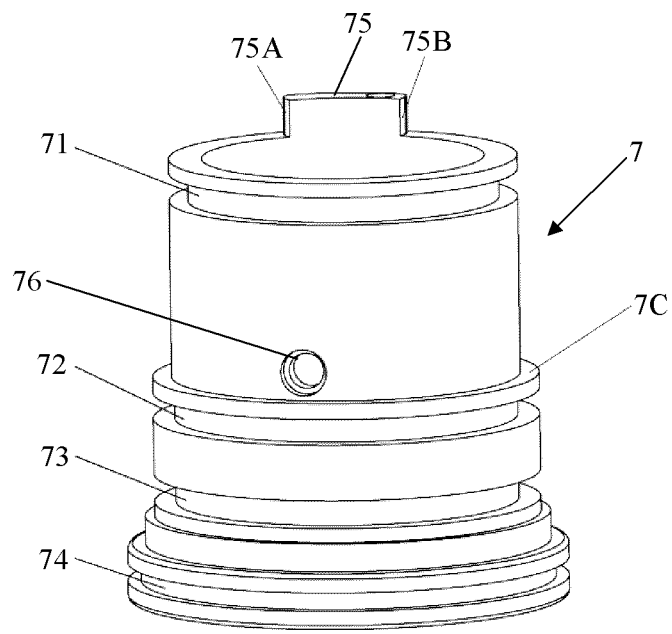
FIG. 7 shows a perspective view of an inner casing in FIG. 2.
Figure 8:
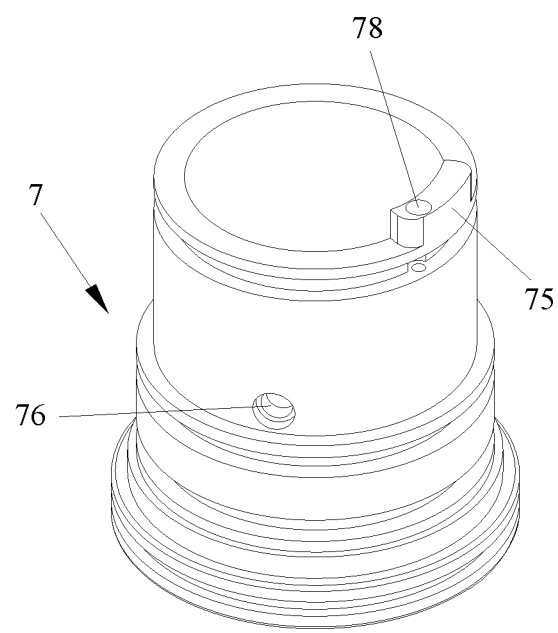
FIG. 8 shows a perspective view of the inner casing in FIG. 7 from another side.
Figure 9:
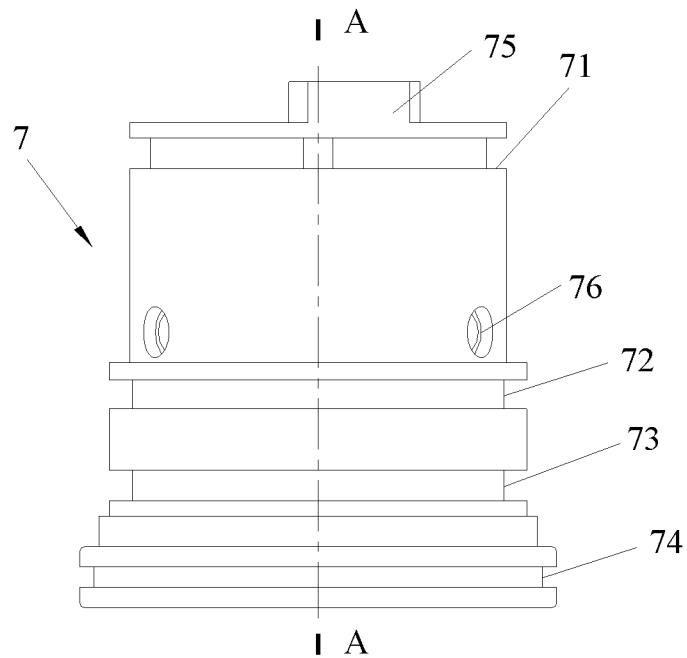
FIG. 9 shows a front view of the inner casing in FIG. 7.
Figure 10:
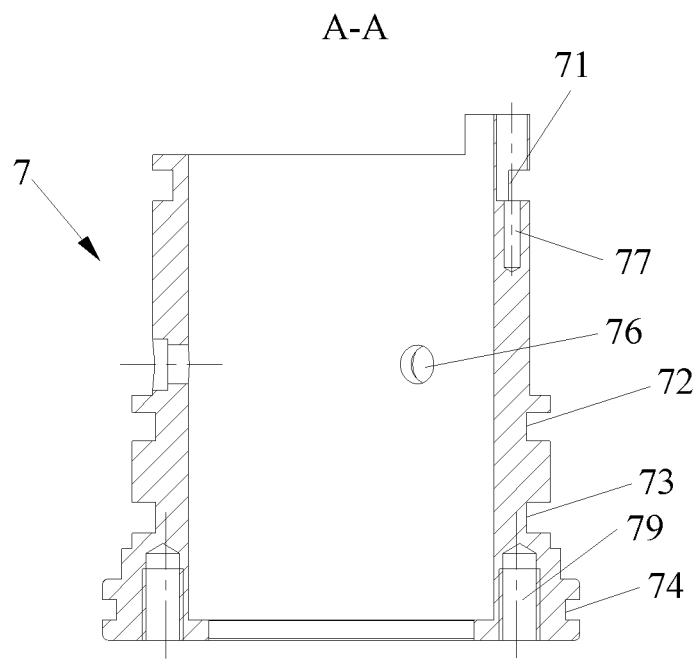
FIG. 10 shows a sectional view of the inner casing in FIG. 7.
Figure 11:
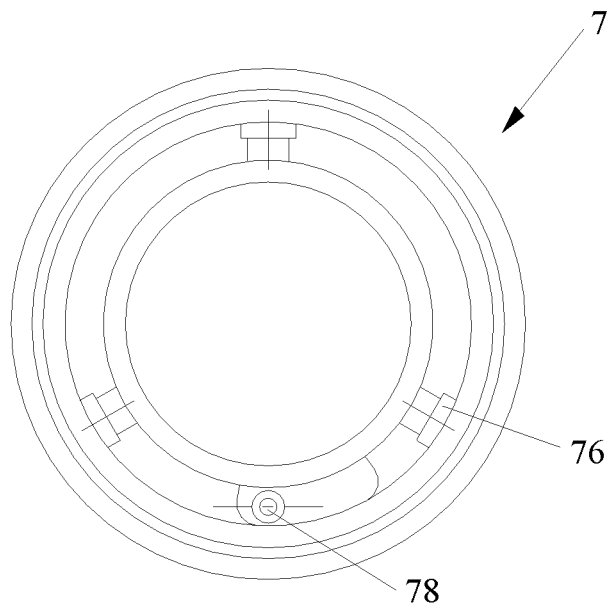
FIG. 11 shows a top view of the inner casing in FIG. 7.

FIGS. 7-11 show the structure of the inner casing 7. FIG. 7 shows the perspective view of the inner casing in FIG. 2. FIG. 8 shows the perspective view of the inner casing in FIG. 7 from another side. FIG. 9 shows the front view of the inner casing in FIG. 7. FIG. 10 shows the sectional view of the inner casing in FIG. 7. FIG. 11 shows the top view of the inner casing in FIG. 7. The inner casing 7 has a cylindrical shape, for connecting with the valve seat 4 and being provided as the foundation for the fixation and connection of other components. As shown in FIGS. 7-11, the inner casing 7 is provided with pin holes 79 and co-axially fixed to the valve seat 4 by positioning pins 3 provided in the pin holes 79. During mounting, the positioning pins 3 are used for the circumferential positioning of the whole pressure control valve on the valve seat 4 and the device requiring pressure control.

The inner casing 7 is provided on its outer surface with a plurality of grooves comprising: the groove 71 on which a restoration spring base is provided and the restoration spring base can be realized in various appropriate forms, for example a locking sleeve 20 or other elements; the groove 72 on which the damping washer 8 is provided and the damping washer 8 is used for sealing as well as for effectively preventing a metal contact between the inner casing 7 and the outer casing 9 for damping; the groove 73 which is used for the fixation with the scale value indication plate 6; and the groove 74 on which the second sealing member 30 is provided. A second washer 10 is provided between the outer casing and a restoration spring 11 contacting therewith. The inner case 7 has a face 7C which is in cooperation with the second washer 10, so as to compensate the length error of the restoration spring 11 by adjusting the thickness or number of the washers 10.

The side wall of the inner casing 7 is provided with holes 76 in which the guiding pins 21 are fixed, for guiding and supporting the spiral guiding member 18. There are three holes 76 provided, which are uniformly distributed along the side surface of the inner casing 7, and of course, the number of the holes can be different.

The inner casing 7 has a flange 75 which is used for the limiting and positioning. Side faces 75A and 75B of the flange 75 are positioning faces. The flange 75 is provided with a hole 78 which axially extends along the inner casing 7, for accommodating a top pin 13. A blind hole 77 is provided below the flange 75, for accommodating a pillar spring 12 standing against the top pin 13.

Figure 37:
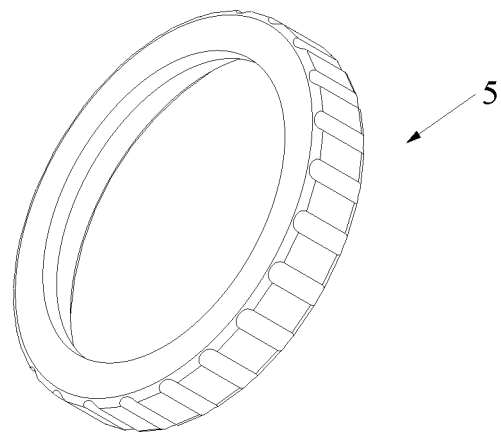
FIG. 37 shows a perspective view of a threaded sleeve in FIG. 2.
Figure 38:
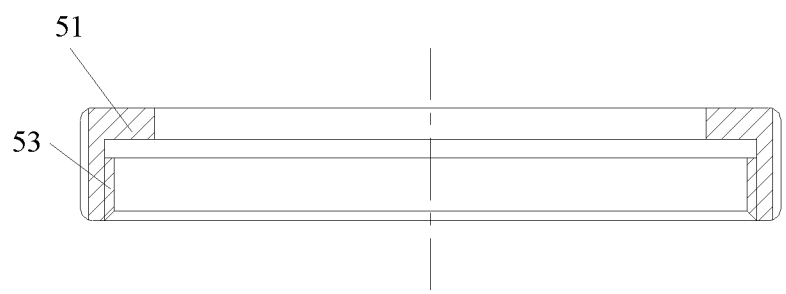
FIG. 38 shows a sectional view of the threaded sleeve in FIG. 37.

FIG. 37 shows the perspective view of the threaded sleeve in FIG. 2. FIG. 38 shows the sectional view of the threaded sleeve in FIG. 37. The threaded sleeve 5 connects the inner casing 7 with the valve seat 4, and locks the relative position between the inner casing 7 and the valve seat 4. The threaded sleeve 5 has an inner thread 53 to connect with the valve seat 4 and a positioning portion 51 to lock the relative position between the inner casing 7 and the valve seat 4. The threaded sleeve 5 is arranged to facilitate the connection between the inner casing 7 and the valve seat 4 and to lock the relative position between the inner casing 7 and the valve seat 4.

Figure 25:
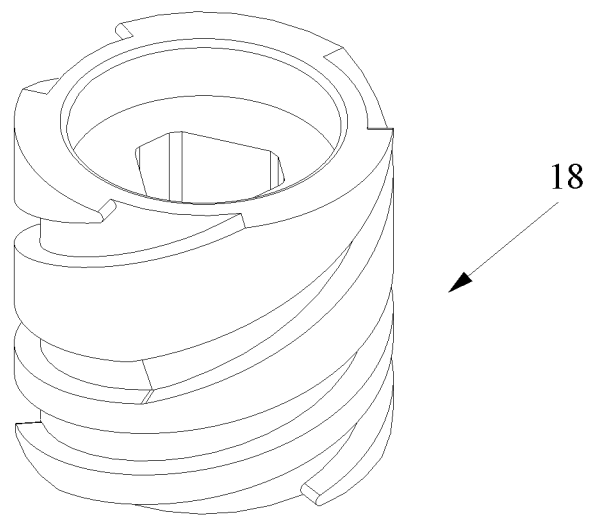
FIG. 25 shows a perspective view of a spiral guiding member in FIG. 2.
Figure 26:
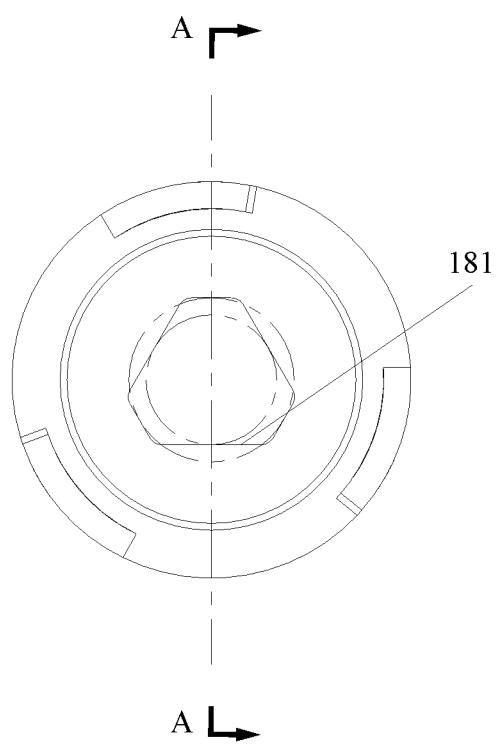
FIG. 26 shows a top view of the spiral guiding member in FIG. 25.
Figure 27:
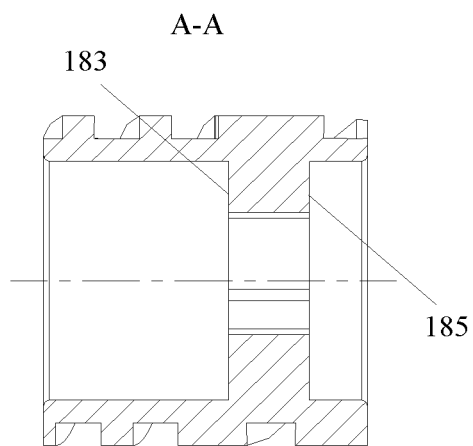
FIG. 27 shows a sectional view of the spiral guiding member in FIG. 26.

FIGS. 25-27 show the structure of the spiral guiding member. FIG. 25 shows the perspective view of the spiral guiding member in FIG. 2. FIG. 26 shows the top view of the spiral guiding member in FIG. 25. FIG. 27 shows the sectional view of the spiral guiding member in FIG. 26. As shown in the figures, the spiral guiding member 18, made of plastic material or metal, is provided with spiral grooves, which may have equal or unequal pitch, but in a preferable embodiment, it is unequal pitch. The guiding pins 21 secured to the inner casing 7 are applied on the spiral grooves, for guiding and supporting the spiral guiding member 18. During adjusting the pressure, the spiral guiding member 18 is made to move axially while the spiral grooves are rotating along the guiding pins 21, which presses or releases the pressure spring 22 to adjust the length of the pressure spring 22.

The spiral guiding member 18 has a second cavity, in which positioning faces 181 are provided for the cooperating connection with the traveling guiding bar 16. The number of the positioning faces 181 may be three, which facilitates the positioning. Of course, the number of the positioning faces 181 may be other value. The upper port of the spiral guiding member 18 has a groove 185. The spiral guiding member 18 has a cavity in the lower portion thereof, which forms a spring base hole for accommodating the pressure spring 22, wherein the pressure spring 22 stands against a top face 183 of the cavity of the spiral guiding member 18 via a first washer 19, so as to avoid the direct contact between metals. The number or the thickness of the washers is adjusted to compensate the length error of the pressure spring 22, such that the value of the pressure set by the pressure control valve is more accurate.

Figure 19:
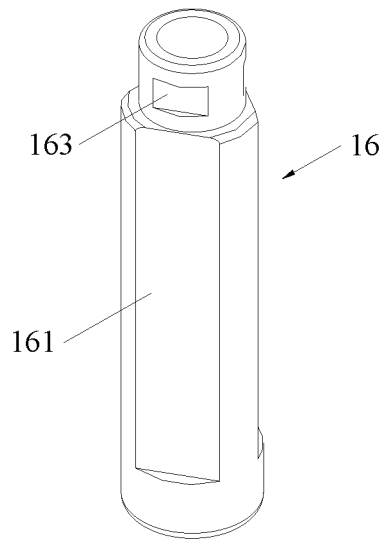
FIG. 19 shows a perspective view of a traveling guiding bar in FIG. 2.
Figure 20:
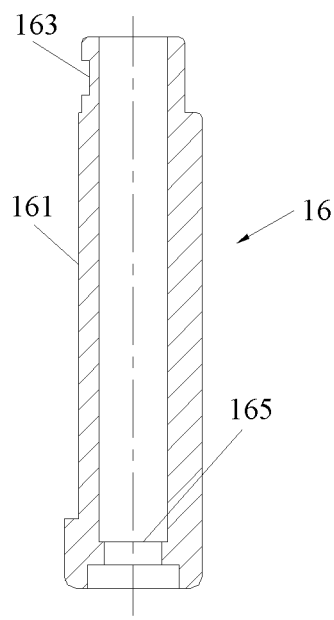
FIG. 20 shows a sectional view of the traveling guiding bar in FIG. 19.
Figure 21:
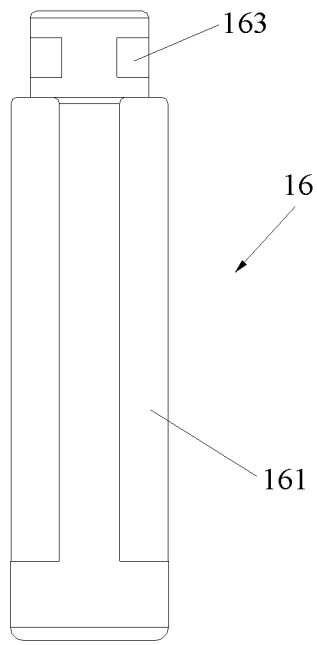
FIG. 21 shows a front view of the traveling guiding bar in FIG. 19.

FIGS. 19-21 show the structure of the traveling guiding bar. FIG. 19 shows the perspective view of the traveling guiding bar in FIG. 2. FIG. 20 shows the sectional view of the traveling guiding bar in FIG. 19. FIG. 21 shows the front view of the traveling guiding bar in FIG. 19. The traveling guiding bar 16, made of metal but not limited thereto, is connected with the index plate 14, the spiral guiding member 18 and the valve core 2, and transfers the rotation of the index plate to the spiral guiding member 18.

As shown in the figures, the traveling guiding bar 16 has on its top connection faces 163, and the index plate 14 is fixed to the connection faces 163 by second fastening screws 27 passing through screw holes 148 in the index plate 14. The number of the connection faces 163 may be three, which facilitates the positioning. Of course, the number of connection faces may be other value. Additionally, the index plate 14 can also be connected with the traveling guiding bar 16, and also it is possible to modify the upper portion of the traveling guiding bar 16 to a threaded structure and a hole in an annular flange of the index plate 14 to an inner thread, so as to achieve the thread connection by the cooperation there between.

The traveling guiding bar 16 can bring the spiral guiding member 18 to rotate together circumferentially, and at the same time, the spiral guiding member 18 can move up-and-down along the traveling guiding bar 16 by the driving of the guiding pins 21.

The traveling guiding bar 16 is provided at its lower portion with the positioning faces 161 which cooperate with the positioning faces 181 in the spiral guiding member 18. The traveling guiding bar 16 is hollow, having a cavity therein to accommodate a valve core nut 23 and a first fastening screw 29. The valve core 2 has a threaded rod 2A inserted into the end of the cavity and the threaded rod 2 is connected with the valve core nut 23 located in the cavity and fastened by the first fastening screw 29. With such an arrangement, the connection and position limitation of the valve core 2 can be achieved, facilitating the connection and the adjustment of the valve core 2.

Figure 17:
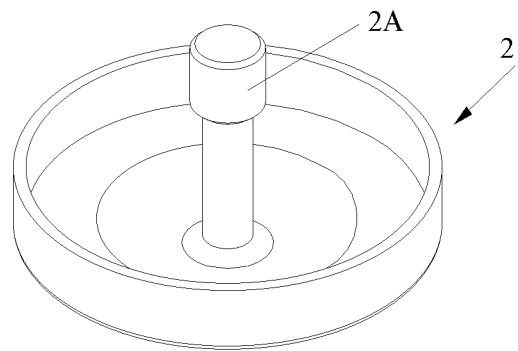
FIG. 17 shows a perspective view of a valve core in FIG. 2.
Figure 18:
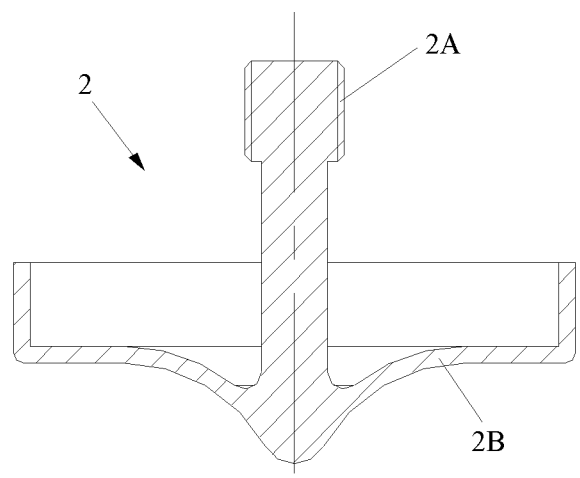
FIG. 18 shows a sectional view of the valve core in FIG. 17.

FIG. 17 shows the perspective view of the valve core in FIG. 2. FIG. 18 shows the sectional view of the valve core in FIG. 17. With the pressure of the pressure spring 22, the valve core 2 cooperates with the air inlet 4A of the valve seat 4 to achieve the sealing. As shown in the figures, the valve core 2 is provided at its upper portion with the rod 2A for the connection with the valve core nut 23. The bottom portion 2B of the valve core 2 has a shape matching to the air inlet 4A of the valve seat 4, so as to seal the air inlet 4A.

The valve core nut 23 connects the valve core 2 with the traveling guiding bar 16, and the first fastening screw 29 can be used to effectively secure and adjust the insertion length of the valve cure 2 into the valve core nut 23.

By using the valve core nut 23 and the first fastening screw 29, the valve core 2 is fixed to the traveling guiding bar 16. The pressure spring 22, according to the extent of compression thereof, limits the magnitude of the pressure of the pressure adjusting valve.

Valve core washers 1 are provided on the valve core 2, avoiding the direct contact between metals. The number or thickness of the valve core washers are adjusted to compensate the length error of the pressure spring 22, such that the value of the pressure set by the pressure control valve is more accurate.

Figure 5:
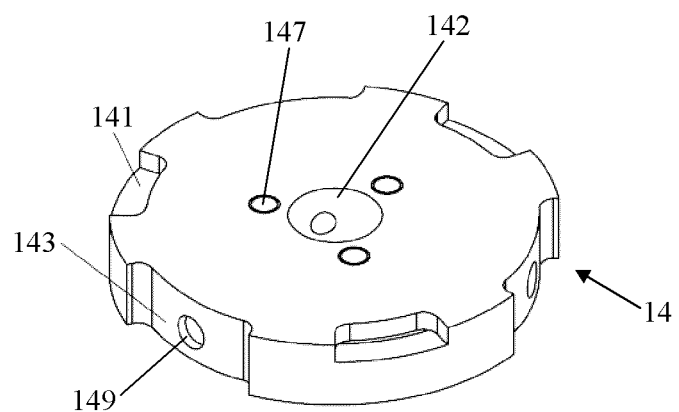
FIG. 5 shows a perspective view of an index plate in FIG. 2.

FIG. 5 shows the perspective view of the index plate in FIG. 2. As shown in the figure, the index plate 14 has the fine-adjusting function to provide the pressure grade division, and the effective position limiting function when being Zero and maximum range, by cooperating with the flange 75 of the inner casing 7. The index plate 14 is provided circumferentially with three assembly slots 143 which are passing-through in the axial direction. Each of the assembly slots has a cylindrical hole 149 at the center, for installation. One mating notch 141 is provided between two of assembly slots 143, for the cooperative positioning with the outer casing 9. The top face of the index plate 14 is distributed with three screw holes 147 in equal interval, for connecting with the screws 26 to be fixed with the pressing board 17 together. A center hole 142 is used for cooperation with the traveling guiding bar 16. Of course, the number of the assembly slots 143 or the screw holes 147 is not limited to three, but could be other value.

Figure 6:
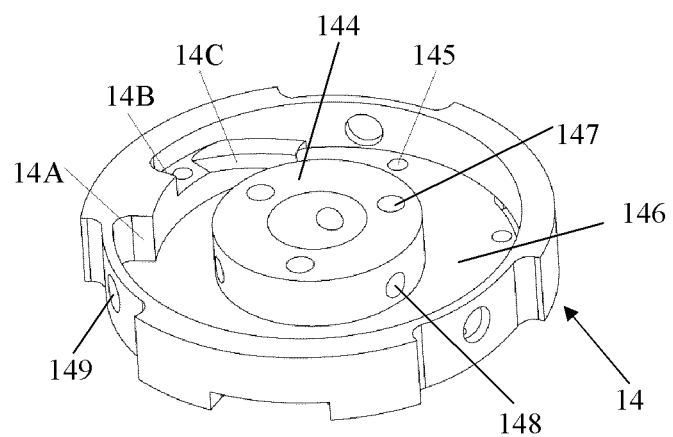
FIG. 6 shows a bottom view of the index plate in FIG. 5.

FIG. 6 shows the bottom view of the index plate in FIG. 5. As shown in the figure, the index plate 14 has an annular flange 144. The flange 144 is distributed on its side surface with three screw holes 148 in equal interval for securing the connection faces 163 of traveling guiding bar 16, and is distributed at its end face with the three screw holes 147 in equal interval. The bottom face of the index plate 14 is circumferentially distributed with spherical pits 145 for cooperating with the top pin 13 to achieve the accurate positioning. By the pillar spring 12, the top spherical surface of the top pin 13 cooperates with the corresponding spherical pit of the index plate to improve the accuracy, simplicity and convenience of the adjustment pressure value. There may be a plurality of the spherical pits 145, with the spherical pits 145 at different positions corresponding to the index plates 14 at different positions, that is, corresponding to different rotation values of the index plate 14, and thus corresponding to the pressing-down values of the pressure spring 22, so as to achieve the accurate positioning. Of course, the effect of the cooperated positioning can also be obtained by using holes.

The index plate 14 has an annular bottom surface 146, a step surface and a transition inclined surface which is located between the annular bottom surface 146 and the step surface. The top pin 13 is rotated on the annular bottom surface 146 with respect to the index plate 14. One end side of the annular bottom surface 146 is provided with a step having the transition inclined surface 14C and the step is provided with a step surface thereon. The end side of the other end of the annular bottom surface 146 is provided with a first positioning side face 14A and the end of the step surface is provided with a second positioning side face 14B. When the first positioning side face 14A is in contact with the positioning face 75A of the inner casing 7, the spiral guiding member 18 reaches the lowest position and the pressure spring 22 has the shortest length. When the second positioning side face 14B of the index plate 14 is in contact with the positioning face 75B of the inner casing 7, the valve core 2 is driven by other components to rise to move away from the air inlet of the valve seat 4, and the pressure control valve is fully opened to directly communicate with the atmosphere. Air enters via the air inlet of the valve seat 4 and is discharged directly via the air outlets. Of course, the positioning face of the index plate may be an inclined annular bottom surface, wherein the annular bottom surface has a beginning end and a termination end corresponding to the positioning side faces 14A and 14B, which also achieve the effect of the first positioning side face 14A and the second positioning side face 14B.

Figure 12:
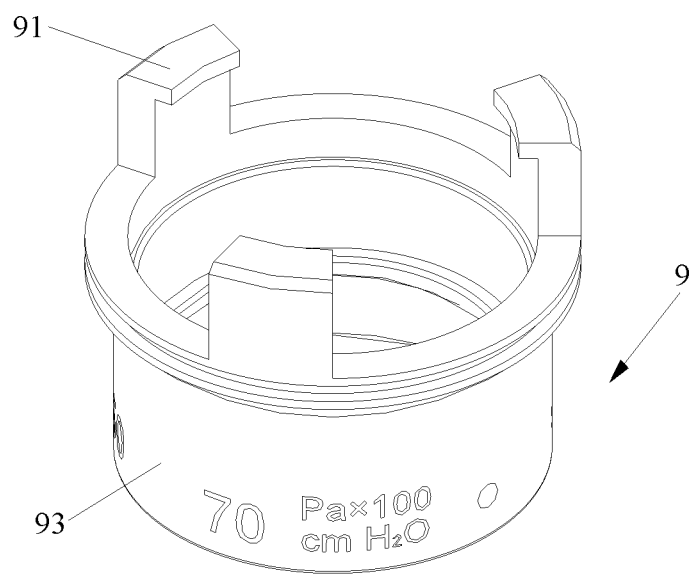
FIG. 12 shows a perspective view of an outer casing in FIG. 2.
Figure 13:
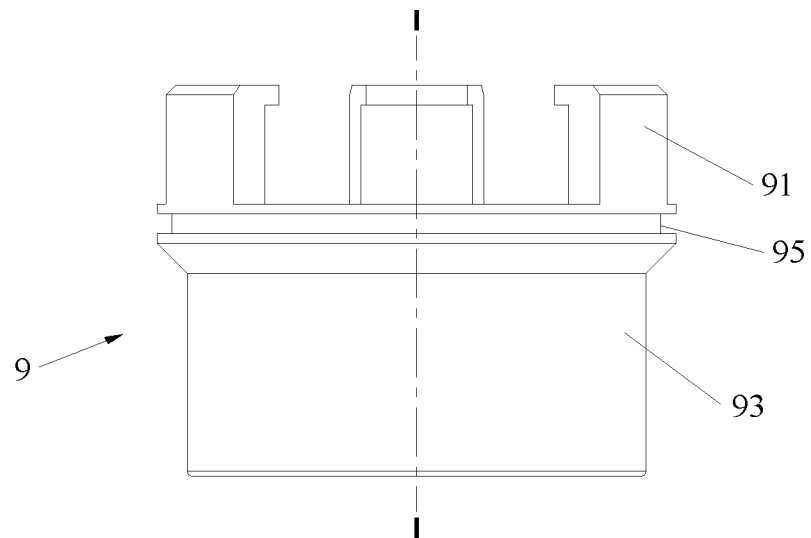
FIG. 13 shows a front view of the outer casing in FIG. 12.
Figure 14:
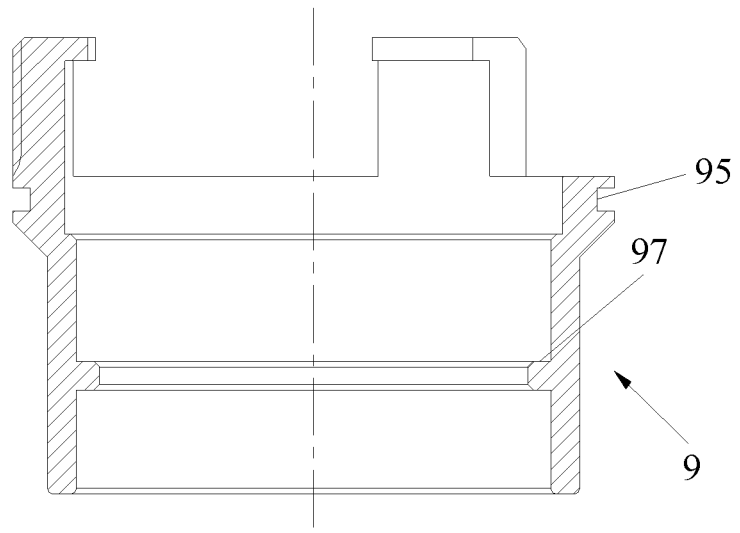
FIG. 14 shows a sectional view of the outer casing in FIG. 12.
Figure 15:
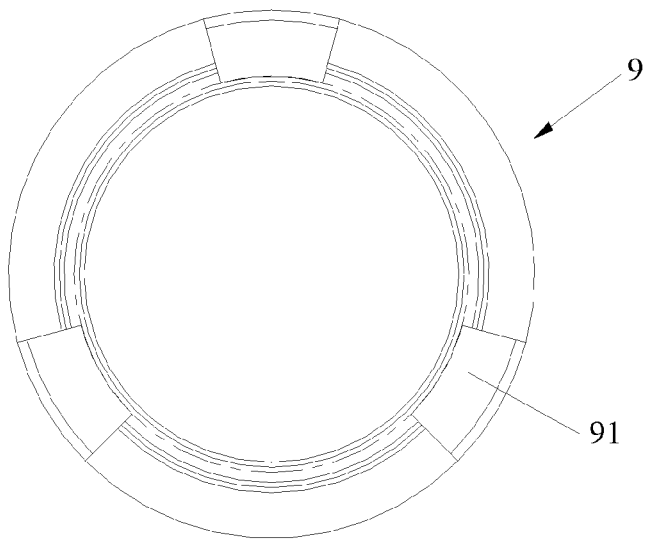
FIG. 15 shows a top view of the outer casing in FIG. 12.

FIGS. 12-16 show the structure of the outer casing 9. FIG. 12 shows the perspective view of the outer casing in FIG. 2. FIG. 13 shows the front view of the outer casing in FIG. 12. FIG. 14 shows the sectional view of the outer casing in FIG. 12. FIG. 15 shows the top view of the outer casing in FIG. 12. As shown in the figures, the outer casing 9 is circumferentially provided in equal interval with three flanges 91, which have outer threads to be connected with the upper cover 15. Each of the flanges 91 protrudes inwards at its top end again to form a driving key so as to be inserted into the mating notches 141 of the index plate 14 to drive the index plate 14 to rotate. A groove 95 is provided below the flanges 91, for the installation and fixation of a fourth sealing member 28. The outer casing 9 is provided therein with an annular positioning flange 97, for supporting the restoration spring 11. A second washer 10 can be sandwiched between the annular positioning flange 97 of the outer casing 9 and the restoration spring 11. A pressure scale of the pressure control valve is marked on an outer side surface 93 of the outer casing 9. The outer casing 9 is fitted rotatably or up-and-down movably over the inner casing 7.

The index plate 14 is provided at its outer circumferential surface with at least one mating notch 141 and the outer casing 9 has driving key(s) which are inserted into the at least one mating notch, which facilitates the outer casing 9 to drive the index plate 14.

Figure 16:
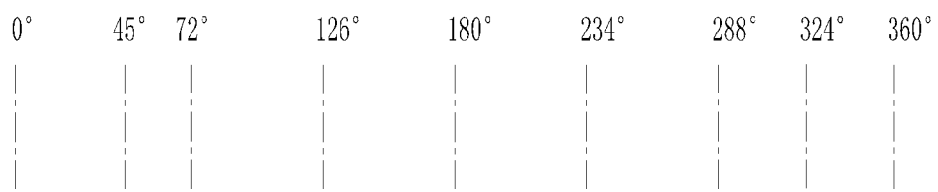
FIG. 16 shows a silk-screen circumferential deploying view of the outer casing in FIG. 12.

FIG. 16 shows a silk-screen circumferential deploying view of the outer casing in FIG. 12. As shown in the figure, corresponding scales are marked on the silk-screen circumferential deploying view of the outer casing, for example, 0 degree, 45 degrees, 72 degrees, 126 degrees, 180 degrees, 234 degrees, 288 degrees, 324 degrees and 360 degrees. These values correspond to different pressing-down values of the pressure spring and different rotation degrees of the index plate 14 and different pits on the index plate 14. Of course, it is not limited to the above values. The particular values can be marked differently, according to the practical situation and combining the selected spring and the distribution of the index pits on the index plate.

Figure 22:
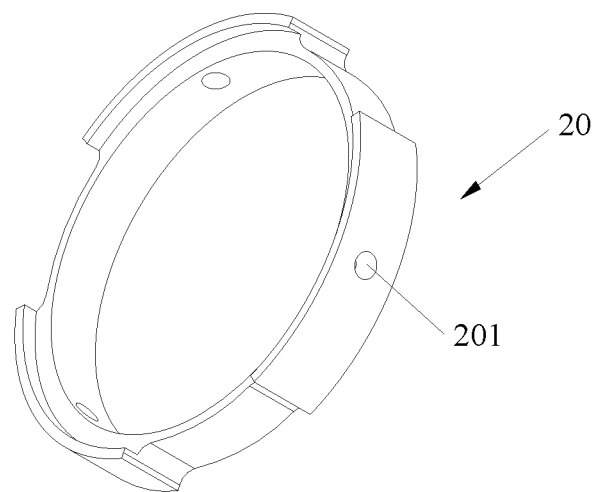
FIG. 22 shows a perspective view of a locking sleeve in FIG. 2.
Figure 23:
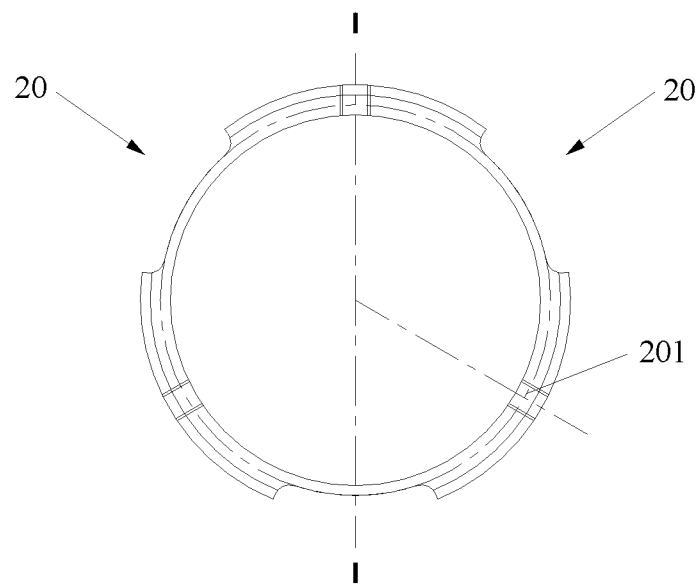
FIG. 23 shows a top view of the locking sleeve in FIG. 22.
Figure 24:
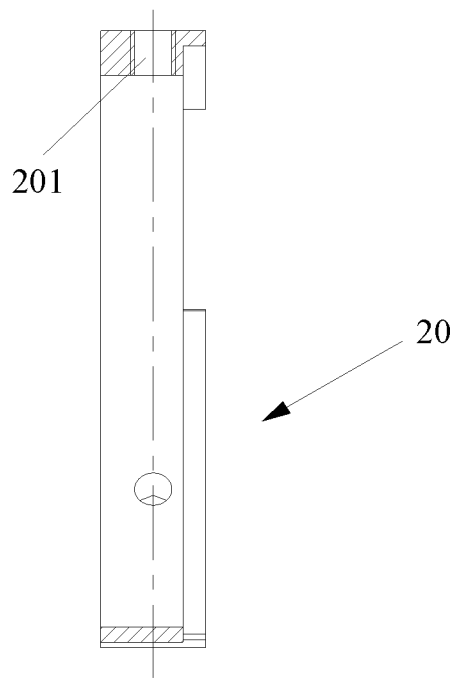
FIG. 24 shows a sectional view of the locking sleeve in FIG. 22.

FIG. 22 shows the perspective view of the locking sleeve in FIG. 2. FIG. 23 shows the top view of the locking sleeve in FIG. 22. FIG. 24 shows the sectional view of the locking sleeve in FIG. 22. As shown in the figures, the locking sleeve 20 is used for securing the position of the restoration spring 11. The locking sleeve 20 is circumferentially distributed with three assembly slots in equal interval which are passing-through in the axial direction. The cylindrical surface of the locking sleeve 20 is circumferentially distributed with three circle holes 201 in total, which are located at the center of the cylindrical surface between the adjacent grooves. Fastening screws 25 pass through the circle holes 201, securing the locking sleeve 20 onto the groove 71 of the inner casing 7. Of course, the number of the assembly slots or the circle holes 201 of the locking sleeve 20 is not limited to three but may be other value.

The restoration spring 11 is a pressure spring, used for providing the restoration function during quickly discharging air. The restoration spring is fitted over the inner casing 7 and pressed between the annular positioning flange 97 of the outer casing 9 and the locking sleeve 20. The second washer 10, which can be pressed between the annular positioning flange 97 of the outer casing 9 and the restoration spring 11, cooperates with the face 7C of the inner casing 7, so as to compensate the length error of the restoration spring 11 by adjusting the thickness or number of the second washers 10. The restoration spring 11, with the top end standing against the locking sleeve 20, produces a downward pressure by the up-and-down movement of its bottom end, which has a restoration design with simply structure and good effect, solving the problem that the operation is not convenient when achieving the function of quickly discharging air.

Figure 28:
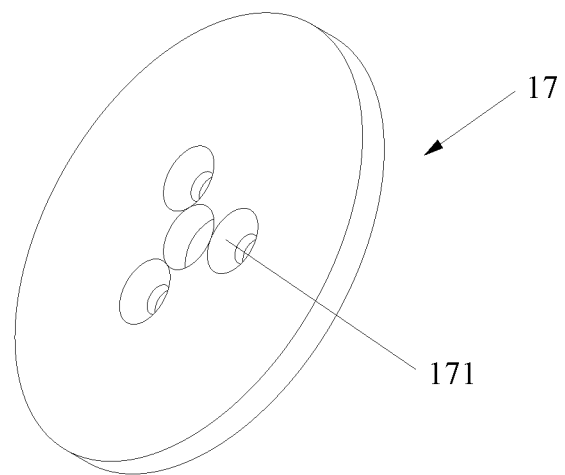
FIG. 28 shows a perspective view of a pressing board in FIG. 2.

FIG. 28 shows the perspective view of the pressing board in FIG. 2. As shown in the figure, the pressing board 17 is a circle board, covering the index plate 14 and the outer casing 9, and provided thereon with holes 171, so as to be connected with the index plate 14 by screws 26 and secure the relative position of the outer casing 9 and the index plate 14. When quickly discharging air, raising the outer casing 9 or the upper cover 15 can bring the index plate 14 to be raised via the pressing board 17, so as to finally bring the valve core 2 to be raised, performing the quick air-discharging.

Figure 35:
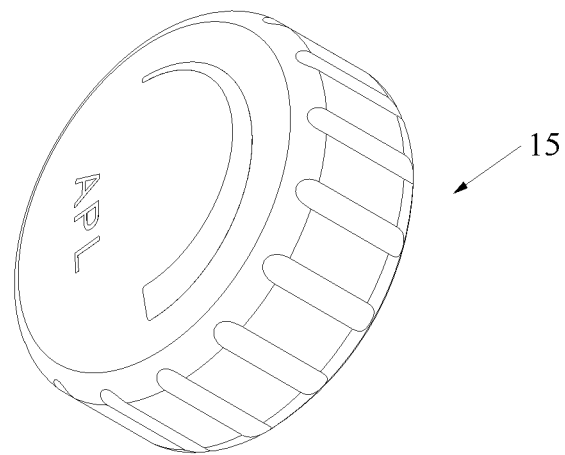
FIG. 35 show a perspective view of an upper cover in FIG. 2.
Figure 36:
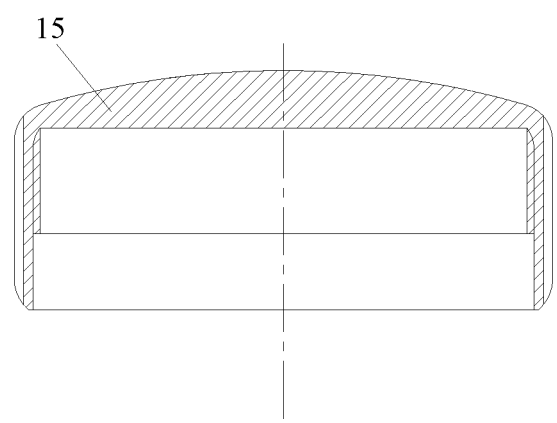
FIG. 36 shows a sectional view of the upper cover in FIG. 35.

FIG. 35 shows the perspective view of the upper cover in FIG. 2. FIG. 36 shows the sectional view of the upper cover in FIG. 35. As shown in figures, the upper cover 15 is fitted over the outer casing 9. The top face of the index plate 14 is flush with the top end of the outer casing 9. Between the top face of the index plate 14 and the inner top face of the upper cover is the pressing board 17 provided, which is fixed together with the index plate 14. The upper cover 15, provided on the pressing board 17, has a thread on its inner side surface, so as to be connected with the outer casing 9. The fourth sealing member 28 is provided between the upper cover 15 and the outer casing 9, for sealing. The upper cover 15 is facilitated to rotate during the operation, so as to bring other components to move.

Figure 32:
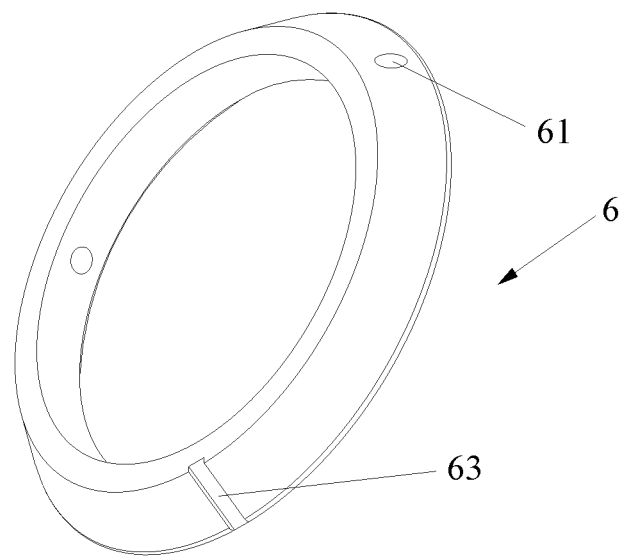
FIG. 32 shows a perspective view of the scale value indication plate in FIG. 2.
Figure 33:
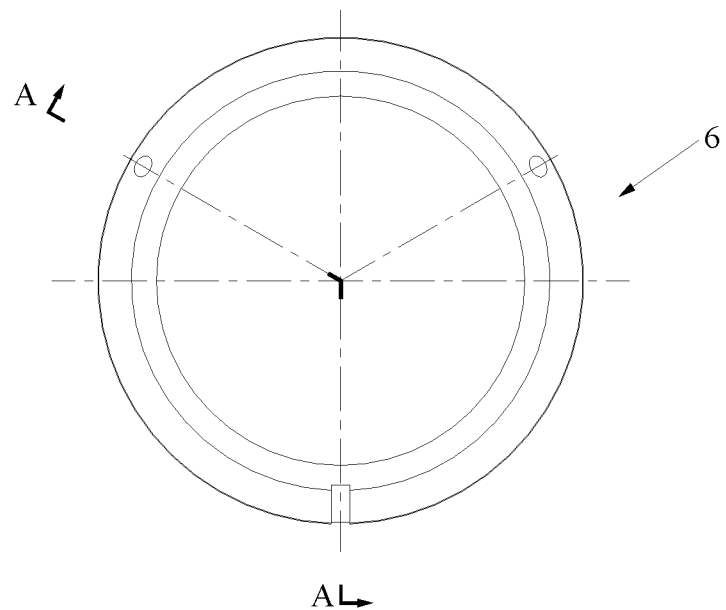
FIG. 33 shows a top view of the scale value indication plate in FIG. 32.
Figure 34:
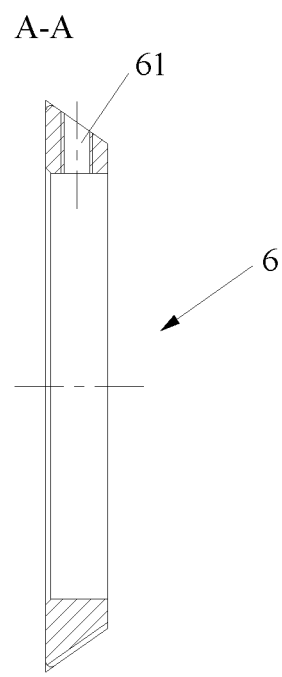
FIG. 34 shows a sectional view of the scale value indication plate in FIG. 32.

FIG. 32 shows the perspective view of the scale value indication plate in FIG. 2. FIG. 33 shows the top view of the scale value indication plate in FIG. 32. FIG. 34 shows the sectional view of the scale value indication plate in FIG. 32. As shown in figures, the scale value indication plate 6 has screw holes 61. Fastening screws (not shown in figures) pass through the screw holes 61, securing the scale value indication plate 6 on the groove 73 of the inner casing 7. The scale value indication plate 6 has a scale groove 63, which cooperates with the values on the outer side surface 93 of the outer casing 9 to indicate the value of the pressure adjustment. The scale value indication plate 6 is provided for facilitating the reading of the pressure value.

The operational principle of the present invention will be described hereinafter.

During adjusting the pressure, the upper cover 15 is rotated which brings the outer casing 9 to rotate together. The outer casing 9 brings, via the flanges 91 at its top, the index plate 14 to rotate. The index plate 14 is fixed together with the pressing board 17 and the traveling guiding bar 16 by the fastening screws 26 and the second fastening screws 27, respectively, such that the pressing board 17 and the traveling guiding bar 16 are rotated synchronously. Through the cooperating plane thereon, the traveling guiding bar 16 brings the spiral guiding member 18 to rotate together. When the spiral guiding member 18 is rotating, the spiral grooves on the spiral guiding member rotate along the guiding pins 21, bringing the whole spiral guiding member 18 to move downwards along the traveling guiding bar to compress the pressure spring 22. Depending on the different rotation angles of the upper cover 15, the length of the pressure spring 22 corresponds to a specific value, that is, to a different opening pressure. A reverse rotation corresponds to extension of the pressure spring 22.

During the rotation, the top pin 13 in the flange of the inner casing 7 is rotated to the spherical pits corresponding to the scales of the index plate and ejected there from under the effect of the pillar spring 12, and the spherical flange of the top pin 13 enters the spherical pit 145. Herein, it is easy to sense that it has rotated to the corresponding scale, such that the positioning of pressure value accuracy of the pressure adjusting valve is improved more exactly and the feeling of the operation is also improved.

When the pressure adjusting valve is rotated to a certain extent, and the index plate 14 is rotated by a certain angle, the spherical surface of the top pin 13 begins to contact the inclined surface 14C of the index plate 14, and when the pressure adjusting valve is rotated continuously, the top pin 13 will jack up the index plate 14, so as to bring the traveling guiding bar 16 and the spiral guiding member 18 to move, causing the valve core 2 moving away from the air inlet, and herein, the pressure adjusting valve is in a Zero state, that is, of communicating with the atmosphere. After the index plate 14 is rotated through a certain angle, the second positioning side face 14B at the side of the inclined surface 14C is in contact with the side face 75B on the flange of the inner casing 7, and thus it is incapable of rotating furthermore, achieving the limiting function of Zero.

After the pressure adjusting valve is rotated to a certain angle in a direction opposite to the direction of the Zero state, the first positioning side face 14A on the index plate 14 is in contact with the side face 75A on the flange of the inner casing 7, and herein, it can not be rotated furthermore and the pressure reaches a maximum limited pressure. At this time, the spiral guiding member 18 is rotated to the lowest position and the pressure spring 22 has the shortest length.

When the pressure adjusting valve is under a pressure with any value, the upper cover 15, when being raised upwards, brings the outer casing 9, the index plate 14, the pressing board 17 and the traveling guiding bar 16 to be raised together, and at the same time, the traveling guiding bar 16 brings the valve core 2 to be raised, causing the valve core 2 to move away from the air inlet. Herein, the pressure adjusting valve has a state identical to the Zero state, i.e., achieving the quick air-discharging. During the raising process, due to the upper end of the restoration spring 11 being limited by the locking sleeve 20, the outer casing 9 compresses the restoration spring 11 and is restored in the downward direction under the pressure of the restoration spring 11. Under the effect of the restoration spring 11, the pressure adjusting valve returns to the state before the raising.

From the above description, it can be seen that the present invention achieves the following technical effects: the positioning and limitation of the pressure adjusting valve according to the present invention are simpler, more effective and accurate, such that the pressure value is more accurate. The function of quick air-discharging is realized more effectively and conveniently.

The above description is only preferable embodiments of the present invention, which are not used to limit the present invention. For those skilled in the art, the present invention may have various changes and variations. Any amendments, equivalent substitutions, improvements and so on within the spirit and principle of the present invention are all included in the scope of protection of the present invention.

What is claimed is:

1. A pressure control valve, comprising:
a cylindrical valve body, having a bottom wall and a side wall, wherein the bottom wall is provided with an air inlet communicating with a device whose pressure is to be limited, the inner side wall comprises at least one guiding pin, and the cylindrical valve body is provided with air outlets communicating to an exhausting system, a valve core, provided within the cylindrical valve body and in air-tight cooperation with the air inlet, a traveling guiding bar, having a lower end connected to the valve core, a covering, fitted rotatably or up-and-down movably over the cylindrical valve body, for driving the traveling guiding bar to rotate or move up-and-down, a spiral guiding member, fitted up-and-down movably over the traveling guiding bar and provided on its outer surface with spiral grooves into which the at least one guiding pin can be inserted, and a pressure spring, having one end pressed against the valve core and the other end standing against the spiral guiding member.

2. The pressure control valve according to claim 1, further comprising a fine adjusting structure including:
an index plate, fixed to the top of the traveling guiding bar and driven by the covering, and an elastic device, provided at the top end of the cylindrical valve body, wherein the index plate has a positioning face which is in contact with the elastic device and the positioning face is distributed with pits or holes for the positioning of the elastic device.

3. The pressure control valve according to claim 2, wherein, the positioning face of the index plate has an annular bottom surface, a step surface and a transition inclined surface located between the annular bottom surface and the step surface, wherein one end side of the annular bottom surface is provided with a first positioning side face, and one end of the step surface is provided with a second positioning side face.

4. The pressure control valve according to claim 2, wherein, the elastic device comprises a top pin and a pillar spring located under the top pin.

5. The pressure control valve according to claim 2, wherein, the covering comprises an upper cover and an outer casing fixedly connected with the upper cover, wherein an outer casing is fitted rotatably or up-and-down movably over the cylindrical valve body, and the outer circumference surface of the index plate is provided with at least one mating notch, and the outer casing has at least one driving key inserted into the at least one mating notch.

6. The pressure control valve according to claim 2, wherein, the top face of an index plate is flush with the top end of the outer casing, and a pressing board is provided between the top face of the index plate and the inner top surface of the upper cover, with the pressing board fixed together with the index plate.

7. The pressure control valve according to claim 5, wherein, the cylindrical valve body is provided at an upper portion thereof with a restoration spring base, the outer casing is provided on an inner wall thereof with an annular positioning flange, and a restoration spring is provided between the restoration spring base of the cylindrical valve body and the annular positioning flange of the outer casing.

8. The pressure control valve according to claim 1, wherein, the traveling guiding bar has a first cavity therein, the valve core has a threaded rod which is inserted into the end of the first cavity, and the threaded rod is connected with a valve core nut positioned within the first cavity and is fastened by a first fastening screw.

9. The pressure control valve according to claim 1, wherein, the end of the spiral guiding member contacting with the pressure spring is formed in a concave shape, so as to form a pressure spring base hole.

10. The pressure control valve according to claim 9, wherein, the outer surface of the traveling guiding bar has at least one traveling guiding bar positioning face extending along the axial direction, the spiral guiding member has therein a second cavity which has therein at least one spiral guiding member positioning face matching with the at least one traveling guiding bar positioning face.

11. The pressure control valve according to claim 10, wherein, the traveling guiding bar is provided at its top with connection faces, the index plate is provided with screw holes, and the index plate is fixed to the connection faces of the traveling guiding bar by second fastening screws.

\* \* \* \* \*